(12) United States Patent
Fenc

(10) Patent No.: US 6,992,301 B2
(45) Date of Patent: Jan. 31, 2006

(54) BEDDING SANITIZATION

(76) Inventor: Jerry Fenc, 413 Guildwood Pkwy., West Hill, ONT (CA) M1E 1R3

( * ) Notice: Subject to any disclaimer, the term of this patent is extended or adjusted under 35 U.S.C. 154(b) by 66 days.

(21) Appl. No.: 10/626,921

(22) Filed: Jul. 25, 2003

(65) Prior Publication Data

US 2005/0017196 A1 Jan. 27, 2005

(51) Int. Cl.
A61L 2/10 (2006.01)
(52) U.S. Cl. .................................. 250/455.11; 422/24
(58) Field of Classification Search .......... 250/455.11, 250/454.11; 422/24, 28, 29, 32, 121, 122
See application file for complete search history.

(56) References Cited

U.S. PATENT DOCUMENTS

| | | | |
|---|---|---|---|
| 3,877,152 A | 4/1975 | Gorman | |
| 4,562,869 A | 1/1986 | Blum | |
| 5,144,146 A | 9/1992 | Wekhof | |
| 5,252,190 A * | 10/1993 | Sekiguchi et al. | 204/157.3 |
| 5,713,137 A | 2/1998 | Fujita | |
| 6,052,846 A | 4/2000 | Patel et al. | |
| 6,576,190 B1 | 6/2003 | Park | |
| 6,811,748 B2 * | 11/2004 | Ettlinger et al. | 422/24 |

FOREIGN PATENT DOCUMENTS

| | | | |
|---|---|---|---|
| CA | 2332669 | | 7/2002 |
| CA | 2335398 | | 7/2002 |
| CA | 2387280 | | 11/2002 |
| CA | 2385170 | | 6/2003 |
| EP | 0 356 896 | | 7/1990 |
| JP | 02005999 A | * | 1/1990 |
| JP | 2000046466 A | * | 2/2000 |
| JP | 2004097467 A | * | 4/2004 |

* cited by examiner

Primary Examiner—Kiet T. Nguyen
(74) Attorney, Agent, or Firm—Senniger Powers

(57) ABSTRACT

A method of operating a facility having beds involves removing bedding (such as pillows, bedspreads, and blankets) from a bed of a facility after departure of a user and irradiating bedding with narrow spectrum radiation to obtain sanitary bedding. The bed is then made up with the sanitized bedding. A sanitizer to effect the method comprises an irradiation chamber and at least one narrow spectrum light for emitting into the chamber. A bedding support is mounted for reciprocation within said chamber between a first terminal position proximate a base of the chamber and a second terminal position part way between the base of the chamber and a top of the chamber. With this arrangement and the top of the chamber acting as a backstop, the sanitizer is particularly suited for sanitizing pillows which may be placed on the bedding support and repeatedly compressed as the bedding support reciprocates.

26 Claims, 8 Drawing Sheets

BEDDING SANITIZATION

BACKGROUND

This invention relates to an approach to, and a device for, sanitizing bedding.

After a guest of a hotel leaves, the linens (comprising the bed sheets and pillow slips) on the bed occupied by the guest are removed and replaced with freshly laundered linens in preparation for receiving the next guest. On the other hand, the heavier bedding—the pillows, blankets, and bedspreads—is normally cleaned only infrequently, typically by being sent out for drycleaning.

This same approach is used in hospitals, with linens of a bed being changed between patients, and heavier bedding being cleaned only infrequently, typically by drycleaning.

A drawback with this approach is that it compromises on the cleanliness of the bedding.

SUMMARY OF THE INVENTION

A user of a bed, particularly if ill, may impart germs not only to the linens, but also to the heavier bedding. In such a situation, if the heavier bedding is not cleaned between users, there is a risk that the next user of the bed may be exposed to these germs and possibly contract an illness.

Recognizing this problem, the present invention provides a method of operating a facility having beds which comprises, after departure of a user of a bed of the facility, removing used bedding from the bed. Bedding is irradiated with narrow spectrum radiation to obtain sanitized bedding and the bed is made up with the sanitized bedding. This method is suited for use with the heavier bedding.

The present invention also provides a sanitizer, comprising an irradiation chamber and at least one narrow spectrum light for emitting into the chamber. A bedding support is mounted for reciprocation within said chamber between a first terminal position proximate a base of the chamber and a second terminal position part way between the base of the chamber and a top of the chamber. With this arrangement and the top of the chamber acting as a backstop, the sanitizer is particularly suited for sanitizing pillows which may be placed on the bedding support and repeatedly compressed as the bedding support reciprocates.

In another aspect, the present invention provides a method of operating a multi-floor facility having beds. A portable sanitizer is brought to a floor of the multi-floor facility. After departure of a user of a bed in a room on the floor of the facility, the used heavier bedding is removed from the bed. The used bedding is then sanitized using the portable sanitizer to obtain sanitized bedding and the bed is made up with the sanitized bedding.

In a further aspect, a method of operating a facility having beds comprises, after departure of a user of a bed of the facility, removing used bedding from the bed. Bedding is sanitized in any suitable manner (i.e., by radiation or otherwise) to obtain sanitary bedding and the bed is made up with the sanitized bedding. A sign is placed on the bed indicating that the sanitized bedding has been sanitized. Again, this method is suited for use with the heavier bedding. In this regard, the sanitized bedding may include a pillow and the sign may comprise a band placed around the pillow.

Other features and advantages of the invention will become apparent from a review of the following description in conjunction with the drawings.

BRIEF DESCRIPTION OF THE DRAWINGS

In the figures which illustrate example embodiments of the invention.

DETAILED DESCRIPTION

The present invention contemplates a method of operating a facility having beds. Such a facility could be a hotel, a hospital, or even an airplane where the seats of the plane act as beds for travellers. The method involves removing used bedding from a bed of the facility after departure of a user. The used bedding, or other bedding, is sanitized by irradiating the bedding with narrow spectrum radiation, such as ultraviolet ("UV") radiation. To provide more thorough sanitization, during the irradiation air may be circulated about the bedding. Additionally, if the bedding is compressible, the bedding may be repetitively compressed and relaxed during irradiation. The bed is made up with the sanitized bedding.

This approach is particularly suited to heavier bedding, such as blankets, pillows, and bedspreads, which is not amenable to regular laundering. So that the method may best ensure a healthy environment, used bedding may be replaced with sanitized bedding every time a new user of the bed departs. A user of the bedding may be assured of this healthier environment if, after making up the bed with the sanitized bedding, a sign is placed on the bed which indicates that the sanitized bedding has been sanitized. In this regard, where the sanitized bedding includes a pillow, the sign may be in the form of a band placed around the pillow.

The repetitive compressing and relaxing of compressible bedding is particularly suitable where the bedding comprises pillows. In this regard, it may be helpful in dislodging germs from the pillows if they are compressed to about one-half their relaxed height.

Where the bedding comprises a blanket or a bedspread, sanitization may be facilitated by moving a narrow band radiation source (for example an ultraviolet light) along opposite sides of the blanket or bedspread at a stand-off from the blanket or bedspread. This may be accomplished by draping the blanket or bedspread over a supporting rod prior to exposing the bedding to narrow band radiation. In such instance, a narrow band radiation source may be moved under the rod.

Where the facility is a multi-floor building, such as a hotel or hospital, it may be more cost effective to implement the method with one or more portable sanitizers that may be deployed on each floor to receive and sanitize used bedding as it is removed from each bed. Bedding, once sanitized, may then be returned to the bed from which it was removed, or find its way onto another bed.

A suitable sanitizer to effect the described method for compressible bedding, such as pillows, is shown in the figures.

Figure 1:
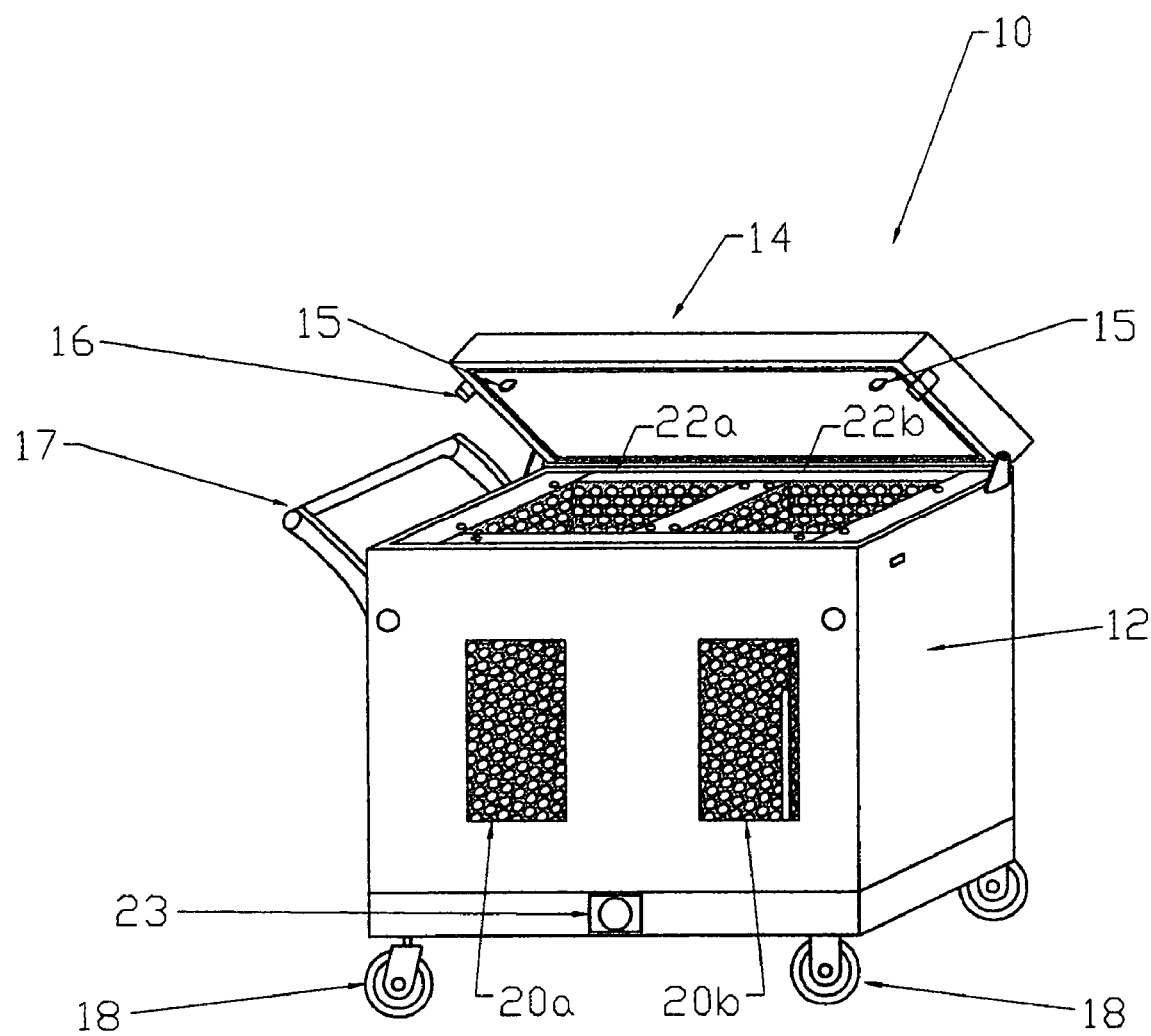
FIG. 1 is a perspective view of a sanitizer made in accordance with this invention.

Turning to FIG. 1, a sanitizer 10 has a cabinet 12 with a tiltable lid 14 which, for reasons which will become apparent, acts as a backstop for bedding inside the sanitizer. The lid may have latching tabs 15 and opening handles 16. The cabinet may be provided with a handle 17 and wheels 18 to make the sanitizer 10 portable. Two UV opaque windows 20a, 20b may be provided to allow viewing of irradiation chambers 22a, 22b, respectively, inside cabinet 12. A butterfly valve 23 allows ambient air to be admitted into cabinet 12 when the ambient air pressure exceeds that inside the cabinet.

Figure 2:
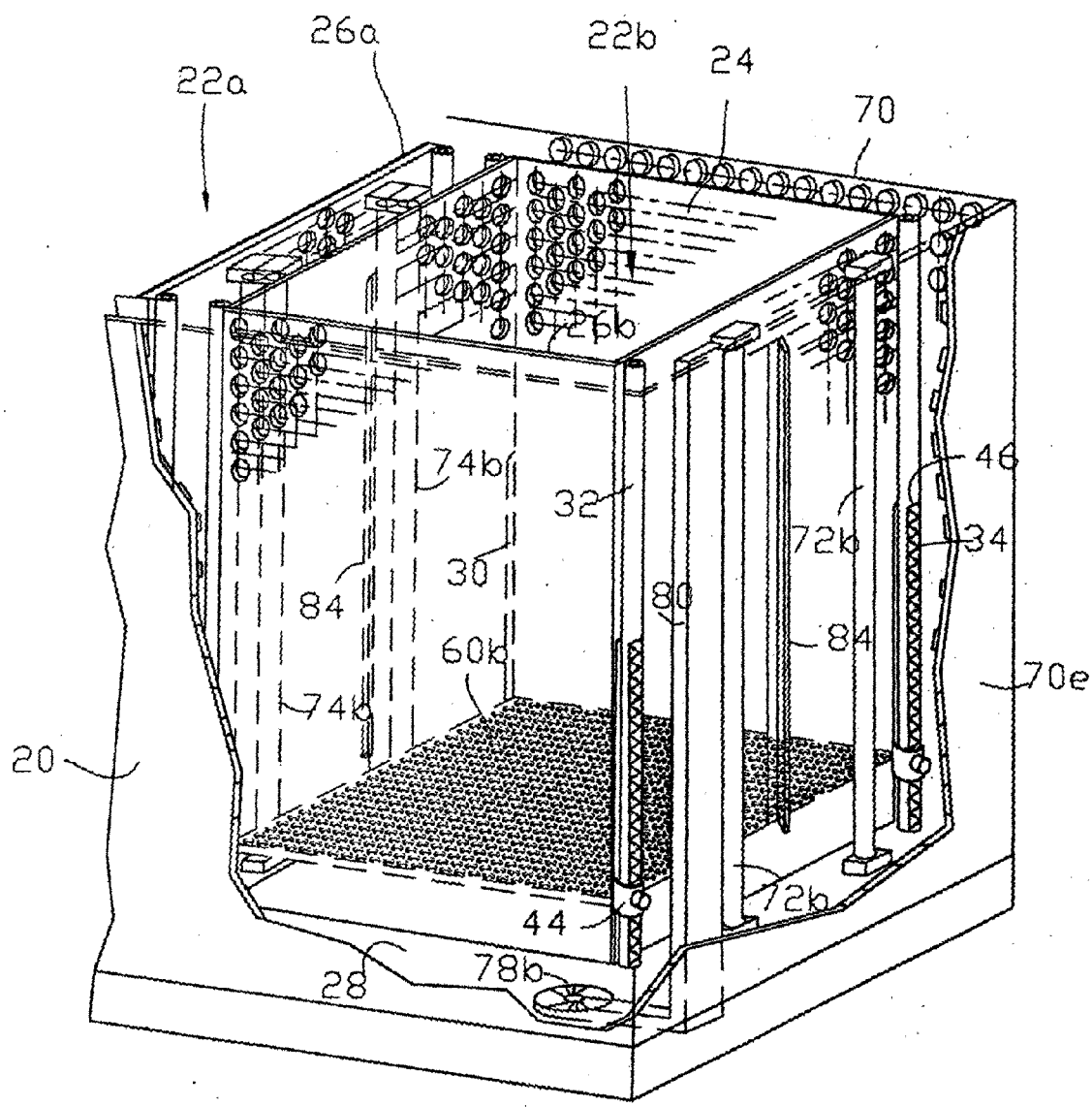
FIG. 2 is a partially broken away perspective view of the sanitizer of FIG. 1.
Figure 4:
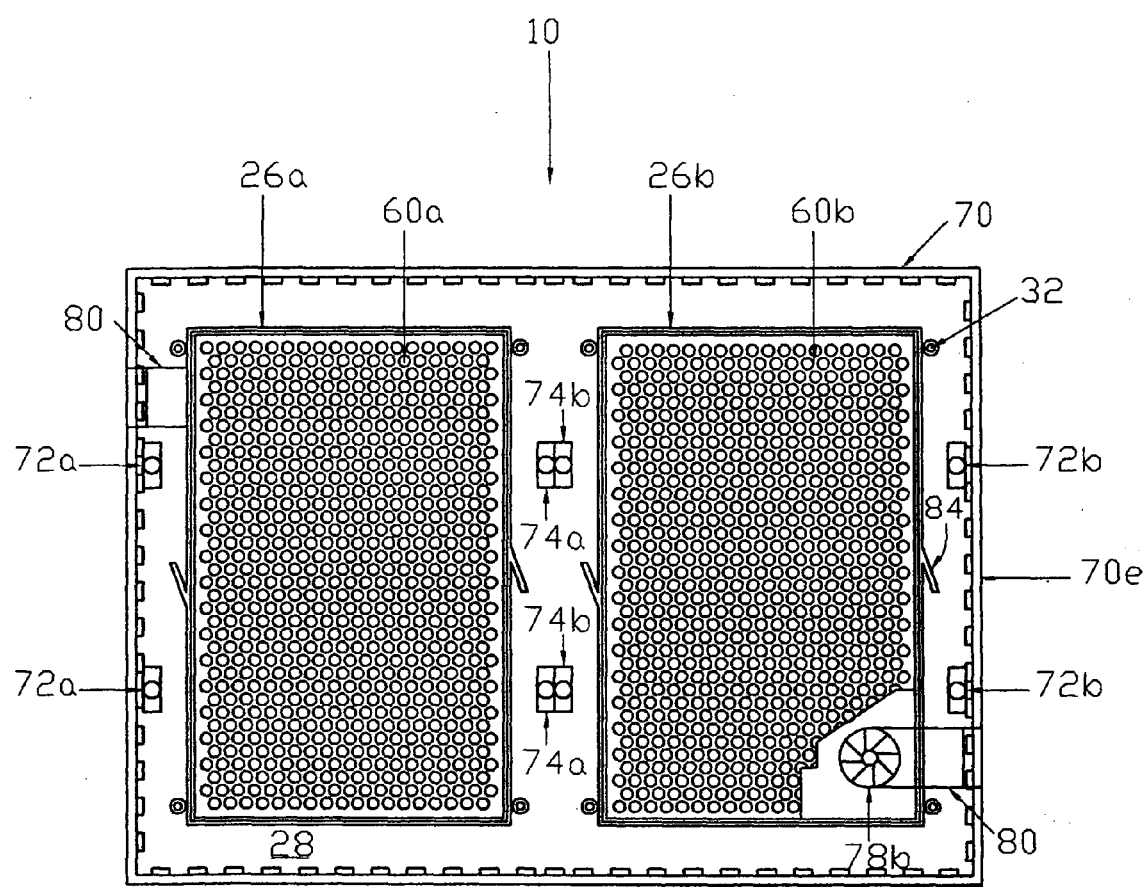
FIG. 4 is a top plan view of a portion of the sanitizer of FIG. 1.
Figure 6A:
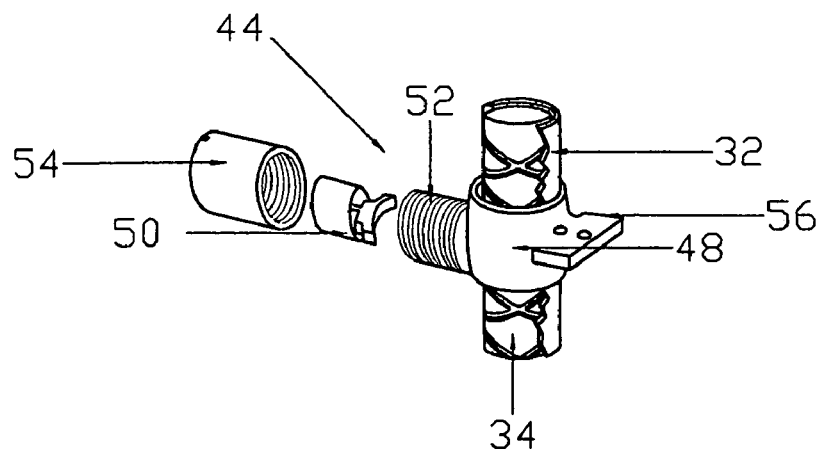
FIG. 6A is an exploded perspective break out view of a portion of the sanitizer of FIG. 1, FIGS. 6B and 6C are schematic side and top plan views of the portion of the sanitizer shown in FIG. 6A, FIGS. 7A and 7B are schematic views illustrating operation of the sanitizer of FIG. 1.
Figure 6B:
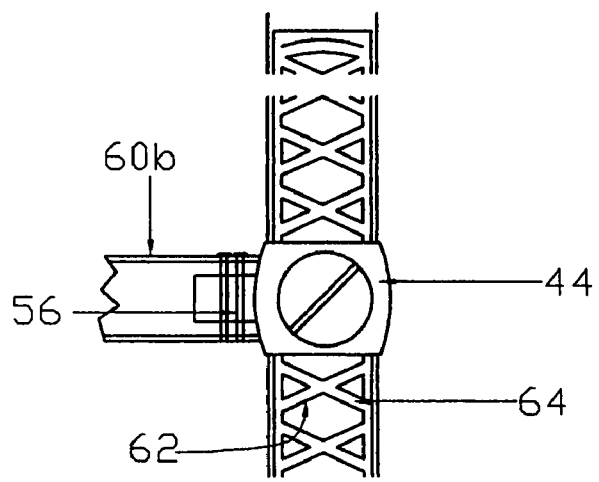
Figure 6C:
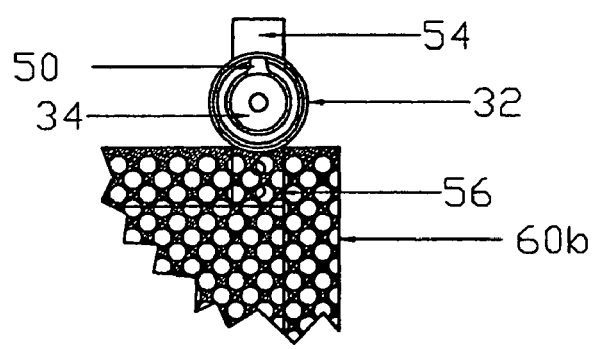

Turning to FIGS. 2 and 4, irradiation chamber 22b is defined by four perforated walls 24 joined at their corners to form a box 26b that is supported on the floor 28 of cabinet 12. The walls 24 may be made of stainless steel. There is a gap 30 extending along each corner of box 26b from the base of the box to approximately one-half the height of the box. A sleeve 32 extends along each corner of the box 26b and is affixed to the cabinet floor 28 and box 26b itself. With reference to FIGS. 6A, 6B, and 6C along with FIG. 2, each sleeve 32 houses a screw 34 that is partially threaded along its length. The screws 34 may be made of carbon steel alloy C-1045, which does not require lubrication.

Figure 5:
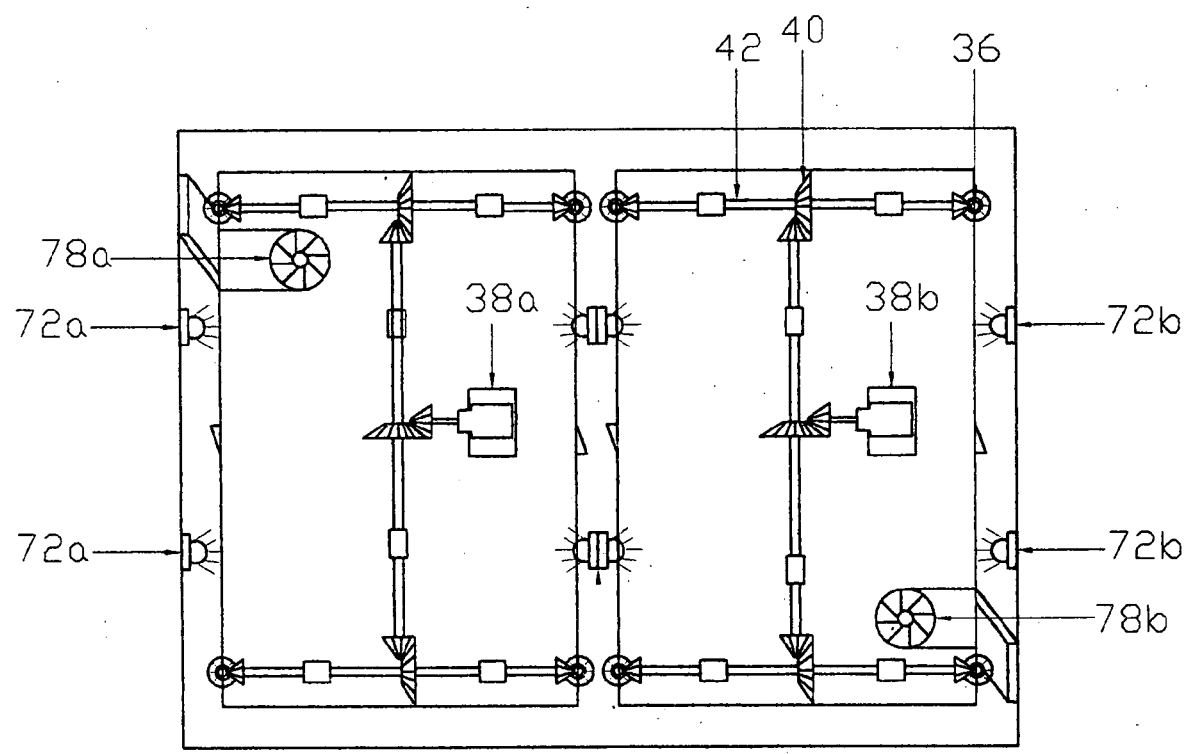
FIG. 5 is a schematic bottom view of the sanitizer of FIG. 1.

With brief reference to FIG. 5, each screw 34 extends through floor 28 and terminates in a bevel gear 36. Each face gear is driven by a motor 38b through a series of bevel gears 40 and shafts 42.

Each sleeve 32 has an axially directed cut out 46 extending from its base to approximately one-half the height of box 26b. This cut out faces away from box 26b and exposes the threads of screws 34. An annulus 48 of a lifting assembly 44 surrounds each sleeve 32 and a tooth 50 fitted into a tube 52 extending from an annulus 48 engages the threads of a screw 34. A cap 54 threaded onto the tube 52 retains the tooth 50 in position. An inwardly directed flange 56 extends from annulus 48 through a gap 30 in the corner of box 26b.

The flange 56 of each of the four annuli 48 is joined to a corner of a perforated bedding support 60b.

Figure 8:
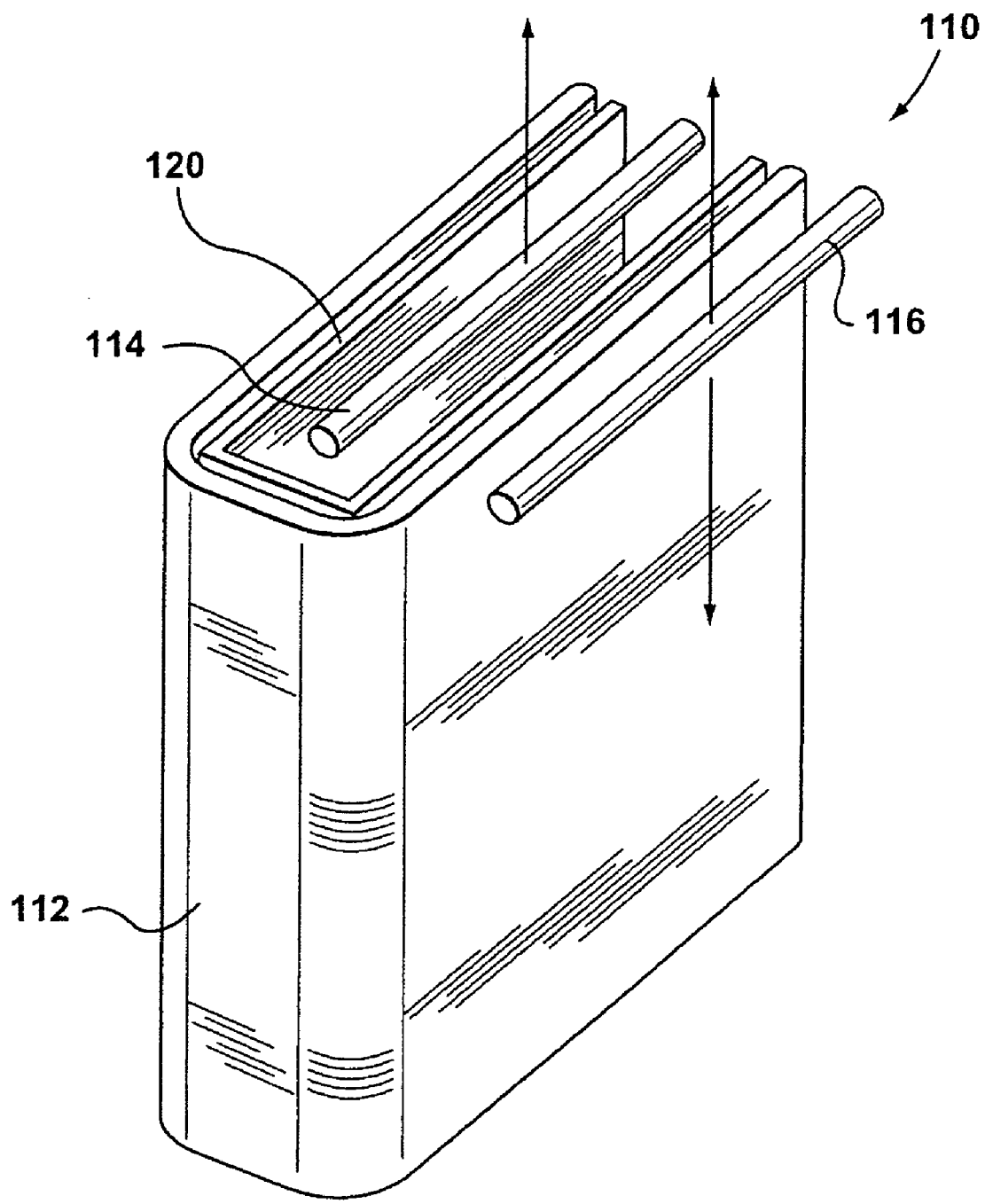
FIG. 8 is a schematic view of a sanitizer made in accordance with another embodiment of this invention.

Referencing FIG. 6B, each of the four screws is threaded with a first spiral thread 62 and a second spiral thread 64 arranged to form a "FIG. 8" pattern along the screw. The first and second spiral threads 62, 64 meet at an inner end of the screw 34 at the top of cut out 46, as seen in FIG. 6B and at the base of the screw (not shown).

The inner face of the walls 70 of cabinet 12 is high gloss and embossed. Walls 70 may be fabricated of aluminum. A first pair of UV lights 72b extends between an end wall 70e of cabinet 12 and an adjacent wall 24 of box 26b. A further pair of UV lights 74b extends between adjacent walls of box 26b of irradiation chamber 22b and box 26a of radiation chamber 22a. The UV lights emit narrow spectrum radiation at a germicidal wavelength, e.g., 2,537 Angstroms.

A fan 78b extends through floor 28 of cabinet 12 and forces air into a chimney 80 and through a side opening 82 (FIG. 3) of the chimney into the gap between the cabinet walls 70 and box walls 24. Air deflectors 84 in walls 24 of box 26 deflect air flowing in the space between the cabinet walls 70 and the box walls 24 into the irradiation chamber 22b.

Figure 3:
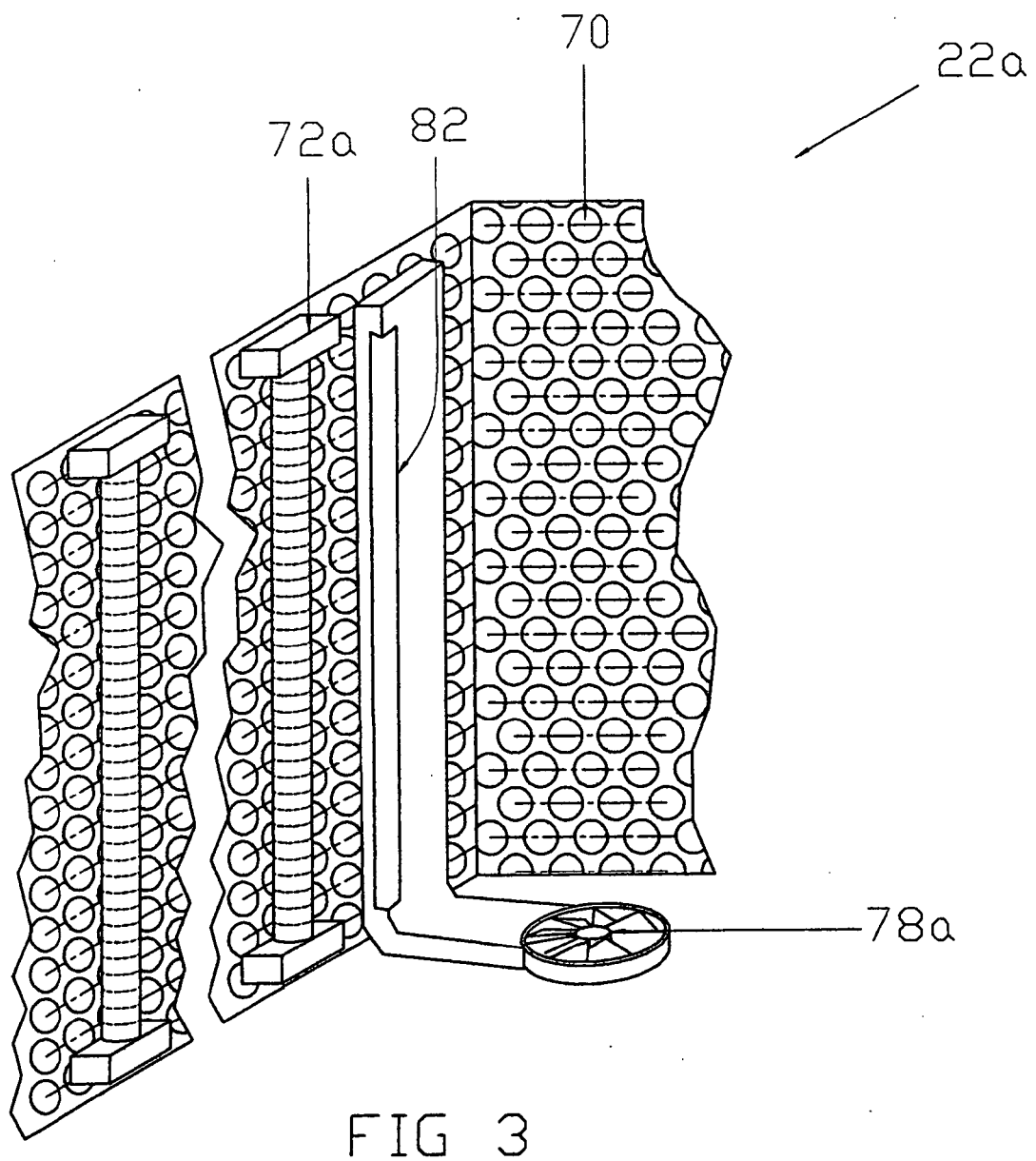
FIG. 3 is another partially broken away perspective view of the sanitizer of FIG. 1.

Irradiation chamber 22a, which is partially shown in FIGS. 2 to 4, is similarly configured.

Figure 7A:
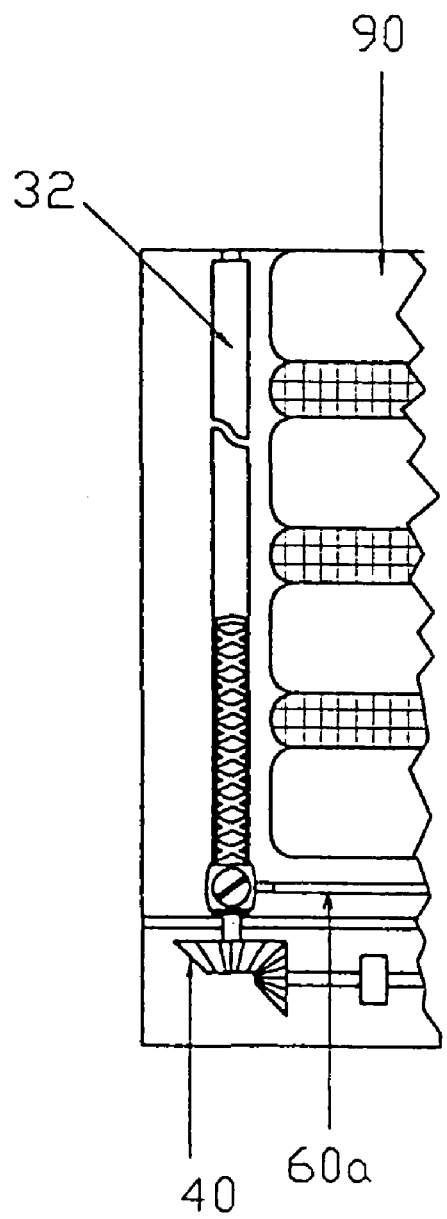
Figure 7B:
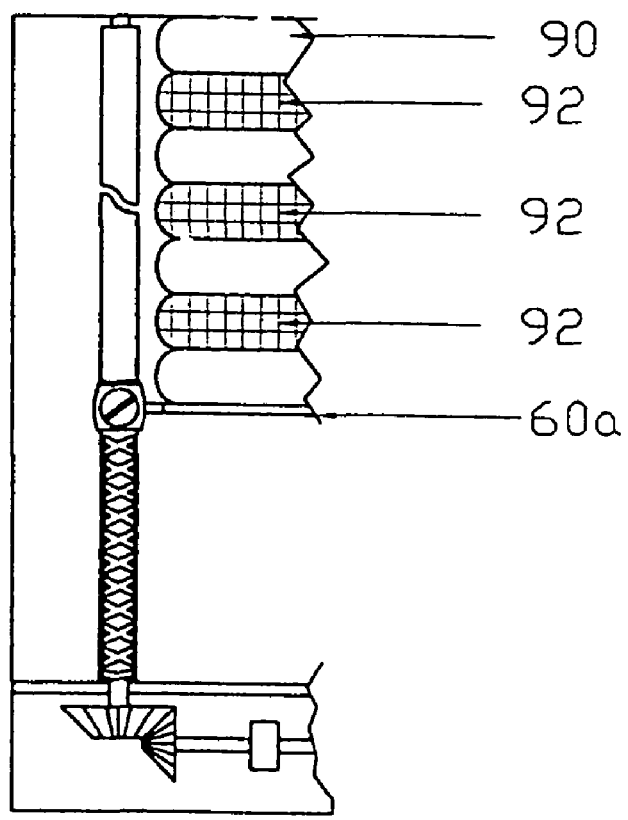

Sanitizer 10 is suited for use in sanitizing compressible bedding, such as pillows. As such, turning to FIG. 7A along with the other figures assuming that the bedding supports 60a, 60b are in their lowermost positions (as illustrated in FIG. 7A) four pillows 90 may be placed into each irradiation chamber 22a, 22b with a perforated spacer 92 being placed between each pair of pillows. The lid 14 of sanitizer 10 may then be closed. Thereafter, UV lights 72a, 72b, 74a, 74b may be illuminated and motors 38a, 38b and fans 78a, 78b activated. With the motors activated, the shaft and bevel gear arrangement rotates face gears 36 and, therefore, each of screws 34 in the same rotational direction. This rotational direction is such that as a screw 34 rotates, its lifting assembly 44 moves upwardly along the first spiral screw thread 62. Thus, the lifting assemblies of each of the four screws surrounding a bedding support act to lift the bedding support 60a, 60b. However, as the bedding support moves upwardly, as illustrated in FIG. 7B, the pillows are compressed between the bedding support and the lid 14, which acts as a backstop.

Once the lifting assemblies reach the inner end of the threaded portion of screws 34 (which is part way between the base and top of the irradiation chamber at the top of the cut-out 46 of sleeves 32), continued rotation of the motors causes the tooth of each lifting assembly to track the second spiral screw thread 64 of the screw 34. In consequence, the lifting assemblies now move downwardly so that the lifting assemblies act to lower the bedding supports 60a, 60b until the bedding supports return to their lowermost position illustrated in FIG. 7A. At this point, the tooth of each lifting assembly begins again to track the first spiral screw thread 62 of the screw 34. As a result, the bedding supports 60a, 60b repeatedly reciprocate as the motors continue to rotate. The reciprocating supports and circulated air assist in ensuring the bedding inside the sanitizer does not overheat.

It will be apparent that with this arrangement, the bedding supports may be reciprocated by simply rotating the motors in one rotational direction. Of course, a less elegant alternative would be to replace the screws with ball screws and control the motors to switch rotational direction at each end of the stroke of the bedding supports.

The sleeve 32 around each screw, having a cut out 46 for tooth 50 which faces away from bedding support 60a, 60b, ensures that the bedding in each irradiation chamber is not snagged by the tooth or screw.

The stroke of the bedding supports may be such that the pillows are compressed to about one-half their relaxed thickness. As the pillows 90 are alternately compressed and relaxed, germs and particles trapped in the pillows are dislodged. All the while, fans 78a, 78b circulate air in the irradiation chambers 22a, 22b. The embossments of the inner surface of walls 70 of cabinet 12 impart turbulence to this circulating air. This turbulent air acts to dislodge loose particles on or in pillows 90. Throughout, the UV lights emit UV radiation into the irradiation chambers which acts to neutralize germs (e.g., bacteria) exposed to the light.

The sanitation of the pillows in the sanitizer 10 may continue for a period of time in order to sufficiently sanitize the pillows. Thereafter, the UV lights may be extinguished and the motors and fans de-activated so that the lid 14 may be opened and the sanitized pillows removed.

The lid 14 of the sanitizer may have a control panel (not shown) used to control parameters of the sanitizer such as the period of sanitization.

The sanitizer 10 may be suitable for use with compressible bedding other than pillows, such as duvets. Where it is desired to sanitize less compressible bedding, a different type of sanitizer could be chosen. For example, in order to sanitize bedspreads or blankets, the sanitizer described in Canadian patent application no. 2,335,398 may be used and the contents of this Canadian application are hereby incorporated by reference.

FIG. 8 schematically illustrates a sanitizer 110 made in accordance with another embodiment of this invention wherein the bedding comprises a blanket or a bedspread 112. Sanitization maybe achieved by moving UV lights 114, 116 along opposite sides of the blanket or bedspread at a stand-off from the blanket or bedspread. This may be accomplished by draping the blanket or bedspread 112 over a support 120 prior to exposing the bedding to UV light. In such instance, a UV light 114 may be moved under the support.

As an alternative to using UV light, far-infrared radiation may be used to sanitize the bedding in the sanitizer. In such instance, the bedding should be first wetted with a small amount of water. This technique is further described in U.S. publication number 2002 00 95946 published Jul. 4, 2002, the contents of which are incorporated by reference herein. A drawback with this approach is that it may take considerable time to dry the bedding.

It is also recognised that for a multi-floor facility (such as a hotel or hospital) having beds, portable sanitizers for the heavier bedding (pillows, blankets, bedspreads) are beneficial, even where the sanitizers sanitize without using radiation. Thus, a portable sanitizer (such as one on wheels) may be brought to a floor of the multi-floor facility. After departure of a user of a bed in a room on the floor of the facility, the used heavier bedding is removed from the bed. The used bedding is then sanitized using the portable sanitizer to obtain sanitized bedding and the bed is made up with the sanitized bedding.

It is further recognised that for a facility having beds, sanitizing of the heavier bedding (pillows, blankets, bedspreads) may be improved, even where sanitization occurs without using radiation. More specifically, after departure of a user of a bed of the facility, used bedding is removed from the bed. Bedding is sanitized in any suitable manner (i.e., by radiation or otherwise) to obtain sanitary bedding and the bed is made up with the sanitized bedding. A sign is placed on the bed indicating that the sanitized bedding has been sanitized. The sanitized bedding may include a pillow and the sign may comprise a band placed around the pillow.

Other modifications will be apparent to those skilled in the art and, therefore, the invention is defined in the claims.

What is claimed is:

1. A method of operating a facility having beds, comprising: after departure of a user of a bed of said facility, removing used bedding from said bed; utilizing at least one source of narrow spectrum radiation, irradiating bedding with narrow spectrum radiation while moving said bedding relative to said at least one source of narrow spectrum radiation to obtain sanitized bedding; and making up said bed with said sanitized bedding.

2. The method of claim 1 wherein said sanitized bedding comprises at least one of a blanket, a pillow, and a bedspread.

3. The method of claim 2 wherein said bedspread is a duvet.

4. The method of claim 2 wherein said facility is a hotel.

5. The method of claim 2 wherein said facility is a hospital.

6. The method of claim 2 wherein said facility is an airplane and said bed is a reclinable seat on said airplane.

7. The method of claim 2 wherein said irradiating with narrow spectrum radiation comprises exposing said bedding to ultraviolet radiation.

8. The method of claim 7 further comprising circulating air about said bedding while exposing said bedding to ultraviolet radiation.

9. The method of claim 1 wherein said removing and making-up occurs every time a new user of said bed departs.

10. A method of operating a facility having beds, comprising: after departure of a user of a bed of said facility, removing used bedding from said bed; irradiating bedding with narrow spectrum radiation to obtain sanitized bedding; and making up said bed with said sanitized bedding, wherein said bedding comprises compressible bedding and further comprising repetitively compressing and relaxing said compressible bedding while exposing said compressible bedding to said narrow spectrum radiation.

11. The method of claim 10 wherein said compressible bedding comprises a pillow.

12. The method of claim 11 wherein said compressing compresses said pillow to about one-half a height of said pillow, when uncompressed.

13. The method of claim 10 wherein said irradiating with narrow spectrum radiation comprises exposing said bedding to ultraviolet radiation.

14. The method of claim 13 further comprising circulating air about said bedding while exposing said bedding to ultraviolet radiation.

15. A method of operating a facility having beds, comprising: after departure of a user of a bed of said facility, removing used bedding from said bed; irradiating bedding with narrow spectrum radiation to obtain sanitized bedding; and making up said bed with said sanitized bedding, wherein said bedding comprises a blanket or a bedspread and wherein said exposing said bedding to ultraviolet radiation comprises moving an ultraviolet light along opposite sides of said blanket or bedspread at a stand-off from said blanket or bedspread.

16. The method of claim 15 further comprising draping said blanket or bedspread over a support prior to exposing said bedding to ultraviolet radiation and wherein said exposing said bedding to ultraviolet radiation includes moving an ultraviolet light under said support.

17. The method of claim 15 wherein said irradiating with narrow spectrum radiation comprises exposing said bedding to ultraviolet radiation.

18. The method of claim 17 further comprising circulating air about said bedding while exposing said bedding to ultraviolet radiation.

19. A sanitizer for bedding, comprising: an irradiation chamber; at least one narrow spectrum light for emitting into said chamber; a bedding support mounted for reciprocation within said chamber between a first terminal position proximate a base of said chamber and a second terminal position part way between said base of said chamber and a top of said chamber.

20. The sanitizer of claim 19 wherein said top of said chamber comprises a backstop to impede any bedding on said bedding support from moving above said top of said chamber while said bedding support reciprocates, such that said any bedding is compressed between said reciprocating bedding support and said backstop when said bedding support moves toward said backstop.

21. The sanitizer of claim 18 further comprising a fan for circulating air within said irradiation chamber.

22. The sanitizer of claim 21 wherein walls of said chamber are embossed to impart turbulence to air circulated in said chamber.

23. The sanitizer of claim 22 wherein said bedding support is mounted proximate its periphery on screws that are threaded along a portion of their length in order to define said first terminal position and said second terminal position.

24. The sanitizer of claim 23 wherein each of said screws is threaded with a first spiral thread and a second spiral thread, said first spiral thread meeting said second spiral thread at an inner end of said screw which is part way between said base of said chamber and said top of said chamber, said first spiral thread and second spiral thread arranged such that a direction of tracing that traces said first spiral thread toward said inner end of said screw traces said second spiral thread away from said inner end of said screw.

25. The sanitizer of claim 24 further comprising at least one motor for driving said screws in said direction.

26. The sanitizer of claim 25 wherein said bedding support comprises a lifting assembly surrounding each of said screws, each lifting assembly supported by a thread of said screw so that rotation of said screws in said direction causes said lifting assemblies to trace one of said first spiral thread and said second spiral thread.

* * * * *